US012472109B2

(12) United States Patent
Blomström et al.

(10) Patent No.: US 12,472,109 B2
(45) Date of Patent: Nov. 18, 2025

(54) DISPOSABLE HYGIENE ARTICLE

(71) Applicant: Essity Hygiene and Health Aktiebolag, Gothenburg (SE)

(72) Inventors: Philip Blomström, Gothenburg (SE); Shadi Ståhl, Mölndal (SE)

(73) Assignee: ESSITY HYGIENE AND HEALTH AKTIEBOLAG, Gothenburg (SE)

( * ) Notice: Subject to any disclaimer, the term of this patent is extended or adjusted under 35 U.S.C. 154(b) by 981 days.

(21) Appl. No.: 16/640,538

(22) PCT Filed: Aug. 22, 2017

(86) PCT No.: PCT/SE2017/050840
§ 371 (c)(1),
(2) Date: Feb. 20, 2020

(87) PCT Pub. No.: WO2019/039977
PCT Pub. Date: Feb. 28, 2019

(65) Prior Publication Data
US 2020/0352796 A1 Nov. 12, 2020

(51) Int. Cl.
*A61F 13/472* (2006.01)
*A61F 13/42* (2006.01)
(Continued)

(52) U.S. Cl.
CPC .......... *A61F 13/4752* (2013.01); *A61F 13/42* (2013.01); *A61F 13/51394* (2013.01);
(Continued)

(58) Field of Classification Search
CPC .... A61F 13/42; A61F 13/475; A61F 13/4751; A61F 13/4752; A61F 13/4753;
(Continued)

(56) References Cited

U.S. PATENT DOCUMENTS 4,598,528 A 7/1986 McFarland et al.
5,387,210 A 2/1995 Murakami
(Continued)

FOREIGN PATENT DOCUMENTS

CL 200902121 11/2009
CN 1244381 A 2/2000
(Continued)

OTHER PUBLICATIONS

International Search Report and Written Opinion for International Application No. PCT/SE2017/050839, dated Apr. 11, 2018, 10 pages.
(Continued)

*Primary Examiner* — Catharine L Anderson
(74) *Attorney, Agent, or Firm* — CANTOR COLBURN LLP

(57) ABSTRACT

Disposable hygiene article is provided including a liquid-permeable topsheet, a liquid-impermeable backsheet, an absorbent core and liquid side barriers arranged substantially along longitudinal edges of the absorbent core and provided to reduce side-edge leakage. The coloured indications are provided on the article along the liquid side barriers to indicate the presence of the liquid side barriers to a user, the coloured indications being provided underneath at least one layer of translucent material so as to be visible through the at least one layer of translucent material while avoiding direct contact with the user's skin.

22 Claims, 5 Drawing Sheets

(51) Int. Cl.

| | |
|---|---|
| ***A61F 13/475*** | (2006.01) |
| ***A61F 13/513*** | (2006.01) |
| ***A61F 13/514*** | (2006.01) |
| ***A61F 13/56*** | (2006.01) |
| *A61F 13/84* | (2006.01) |

(52) U.S. Cl.
CPC .... *A61F 13/51496* (2013.01); *A61F 13/5616* (2013.01); *A61F 2013/8402* (2013.01); *A61F 2013/8497* (2013.01)

(58) Field of Classification Search
CPC .............. A61F 13/476; A61F 13/51394; A61F 13/51496; A61F 13/5616; A61F 2013/15243; A61F 2013/51377; A61F 2013/8497
See application file for complete search history.

(56) References Cited

U.S. PATENT DOCUMENTS

| | | | | |
|---|---|---|---|---|
| 6,632,208 | B1 | 10/2003 | Mizutani | |
| 6,719,742 | B1 | 4/2004 | McCormack et al. | |
| 7,270,651 | B2 * | 9/2007 | Adams | A61F 13/15203 604/385.01 |
| 7,432,412 | B2 * | 10/2008 | Kigata | A61F 13/4751 604/362 |
| 7,824,385 | B2 * | 11/2010 | Ecker | A61F 13/4758 604/385.01 |
| 8,262,633 | B2 * | 9/2012 | Larson | A61F 13/84 604/385.101 |
| 8,563,802 | B2 * | 10/2013 | Nishikawa | A61F 13/511 604/385.04 |
| 8,716,548 | B2 * | 5/2014 | Magee | A61F 13/5638 604/361 |
| 8,946,500 | B2 * | 2/2015 | Hopkins | A61F 13/4753 604/361 |
| 9,011,397 | B2 * | 4/2015 | Hopkins | A61F 13/539 604/385.01 |
| 2002/0016579 | A1 | 2/2002 | Stenberg | |
| 2004/0243087 | A1 | 12/2004 | Kinoshita et al. | |
| 2006/0116653 | A1 | 6/2006 | Munakata et al. | |
| 2010/0191209 | A1 | 7/2010 | Nomoto et al. | |
| 2013/0030401 | A1 | 1/2013 | Heyman | |
| 2014/0343525 | A1 | 11/2014 | Roh et al. | |
| 2015/0080830 | A1 | 3/2015 | Miura | |
| 2015/0297781 | A1 | 10/2015 | Uda et al. | |
| 2016/0331598 | A1 * | 11/2016 | Morrison | A61F 13/47 |

FOREIGN PATENT DOCUMENTS

| | | | |
|---|---|---|---|
| CN | 1436065 | A | 8/2003 |
| CN | 101116643 | A | 2/2008 |
| CN | 101410077 | A | 4/2009 |
| CN | 101677885 | A | 3/2010 |
| CN | 101686880 | A | 3/2010 |
| CN | 104010610 | A | 8/2014 |
| EP | 0581258 | A1 | 2/1994 |
| EP | 1842512 | A1 | 10/2007 |
| EP | 1994917 | A1 | 11/2008 |
| EP | 2163229 | A1 | 3/2010 |
| EP | 2281537 | A1 | 2/2011 |
| ES | 1014477 | U | 4/1991 |
| ES | 2086778 | T3 | 7/1996 |
| ES | 2105209 | T3 | 10/1997 |
| ES | 2173593 | T3 | 10/2002 |
| ES | 1153108 | U | 3/2016 |
| FR | 2268508 | A1 | 11/1975 |
| GB | 2306888 | A | 5/1997 |
| GB | 2433416 | A | 6/2007 |
| JP | 2008148819 | A | 7/2008 |
| RU | 2386424 | C2 | 4/2010 |
| WO | 2007069965 | A1 | 6/2007 |
| WO | 2016068957 | A1 | 5/2016 |

OTHER PUBLICATIONS

International Search Report and Written Opinion for International Application No. PCT/SE2017/050840, dated Apr. 11, 2018, 14 pages.
International Search Report and Written Opinion for International Application No. PCT/SE2017/050841, dated Apr. 11, 2018, 12 pages.
European Application No. 17922191.6-1102; European Office Action dated Nov. 4, 2022; 4 pages.
Colombian Patent Office, Office Action issued Dec. 22, 2021, International Application No. PCT/SE2017/050840, 7 pages.
Federal Service for Intellectual Property, Russia, Official Action issued in Application No. 2020111555(019515), dated Oct. 2, 2020, 13 pages, with English translation.
National Intellectual Property Administration (CNIPA) of the People's Republic of China, Office Action issued in CN 201780093645.6 dated Apr. 6, 2021 (with English translation), 24 pages.
European Patent Office, Extended European Search Report issued in EP Application No. 17922191.6-1102, dated Mar. 2, 2021, 6 pages.
Australian Government, IP Australia, Examination report No. 1 for standard patent application issued in corresponding Australian Application No. 2017428325, dated Aug. 6, 2020, 5 pages.
Federal Service for Intellectual Property, Russia, Official Action and Search Report issued in corresponding Russian Patent Application No. 2020111224/03(018874), dated Aug. 11, 2020, 13 pages, with English Translation.
Australian Government, IP Australia, Examination report No. 1 for standard patent application issued in Australian Patent Application No. 2017428323, dated Aug. 4, 2020, 4 pages.
Federal Service for Intellectual Property, Russia, Official Notification of examination results and Search Report issued in Application No. 2020111223(018873), dated Aug. 11, 2020, 11 pages, with English translation.
Pinzon Pinzon & Asociados, Third Party Submission in Application No. NC2020/0001993 dated May 5, 2019, 19 pages (no English translation available).
Chinese Application No. 201780093645.6; Office Action dated Mar. 28, 2025; 14 pages.
Mexican Application No. MX/a/2020/002005; Office Action with English translation dated Jan. 9, 2025; 14 pages.

* cited by examiner

DISPOSABLE HYGIENE ARTICLE

CROSS REFERENCE TO RELATED APPLICATIONS

This is a U.S. National Phase application of PCT/SE2017/050840, filed Aug. 22, 2017, the disclosure of which is incorporated herein by reference in its entirety for all purposes.

TECHNICAL FIELD

The present disclosure relates to disposable hygiene articles, such as adult incontinence articles, sanitary towels and panty liners or the like, provided with liquid side barriers.

BACKGROUND

Disposable hygiene articles have to meet high requirements. They should for example be discreet, soft and comfortable to wear and at the same time they should have a reliable security against leakage. Such disposable hygiene articles usually comprise a liquid-permeable topsheet, a liquid-impermeable backsheet and an absorbent core arranged between the topsheet and the backsheet.

During the use of disposable hygiene articles there is a risk that bodily discharges such as urine, menstrual fluids or other bodily fluids move on top of the liquid-permeable topsheet and leak past the edges of the article. Although liquid movements can take place in any direction for example in the longitudinal direction or in the transverse direction of the hygiene article, liquid movement in transverse direction of the hygiene article is particularly worrying because only a relatively small liquid movement in the transverse direction may cause the liquid to leak outside the longitudinal side edges of the hygiene article with the result that surrounding articles such as clothing, bedclothes, seat cushions are soiled by discharged liquid. The risk of so-called side-edge leakage is the highest during night, for example when sleeping on the side.

Some known hygiene articles are provided with liquid side barriers along the longitudinal edges of the absorbent core which are intended to reduce the risk of side-edge leakage. It has been found that the proper functioning of such liquid side barriers is highly dependent on the positioning of the hygiene article on the garment.

SUMMARY

It is an aim of the present disclosure to provide a disposable hygiene article provided with liquid side barriers with which an increased sense of security may be achieved.

It is another aim of the present disclosure to provide a disposable hygiene article provided with liquid side barriers that can be manufactured in a relatively simple manufacturing process.

At least one of the above aims may be achieved by a disposable hygiene article or a manufacturing process as defined in the independent claims.

According to an aspect of the present disclosure, a disposable hygiene article is provided, comprising a liquid-permeable topsheet, a liquid-impermeable backsheet and an absorbent core arranged between said topsheet and said backsheet, the absorbent core defining a longitudinal centre axis which extends substantially in the middle of the core in longitudinal direction L of the article. The disposable hygiene article is adapted to be releasably attached to a garment, such as underpants or briefs. In use of the article the topsheet is facing the crotch area of a user and the backsheet is facing away from the crotch area of the user.

The article further comprises liquid side barriers arranged substantially along longitudinal edges of said absorbent core and provided to reduce or minimize side-edge leakage. Coloured indications are provided on the article along said liquid side barriers to indicate or highlight the presence of said liquid side barriers to a user, said coloured indications being provided underneath at least one layer of translucent material, i.e. at least one layer of the article which is/are in a translucent material, so as to be visible through said at least one layer of translucent material while direct contact with the user's skin is avoided.

It has been found, surprisingly, that by providing coloured indications on the hygiene article to indicate or highlight the presence of the liquid side barriers to the user, an increased leak protection is signaled to the user, and thus an increased sense of security may be achieved. By the provision of these coloured indications underneath at least one layer of translucent material, direct contact with the user's skin and hence transfer of the colour onto the user's skin can be avoided.

In embodiments according to the present disclosure, at least parts of said coloured indications may be provided on longitudinal edge portions of said topsheet, preferably printed on a garment facing side of the topsheet, which implies that the topsheet forms one of the layers of translucent material. Printing on the garment facing side of the topsheet has the advantage that the coloured indications may be applied in the same step as the printing step by which a further coloured indication is applied on the garment facing side of the topsheet, which further coloured indication may for example be located in an absorption area of the article in between the longitudinal edge portions of the topsheet and be provided to indicate a so-called "wetting area" to the user.

In embodiments according to the present disclosure, at least parts of said coloured indications may be provided on longitudinal edge portions of said backsheet. Said coloured indications may for example be provided partly on the topsheet and partly on the backsheet.

In embodiments according to the present disclosure, said liquid side barriers may form part of side layers which are arranged substantially along the longitudinal edges of the absorbent core. The side layers may comprise, on each side, a portion which extends above the respective coloured indication, said portion preferably forming a second layer of translucent material through which the coloured indication on that side is visible, in certain embodiments.

In embodiments according to the present disclosure, said portions of the side layers may extend above the topsheet while being loose therefrom. It has been found that portions of such side layers which extend above the topsheet while being loose therefrom may form, or form part of, the liquid side barriers and/or assist in reducing the risk of side-edge leakage.

In embodiments according to the present disclosure, the liquid side barriers may be provided for being at least partly raised to a substantially upright position in use. The raising of at least part of the side barriers in use may enhance the barrier and thus further reduce side-edge leakage.

In embodiments according to the present disclosure, the hygiene article may further comprise flexible side flaps arranged on opposite sides of the absorbent core and provided for attaching the article to a garment, for example by being folded around a crotch part of said garment.

In embodiments according to the present disclosure, the liquid side barriers may be provided for being at least partly raised by folding said flexible side flaps to a position in which said hygiene article is secured to said garment.

In embodiments according to the present disclosure, the liquid side barriers may be provided for being at least partly raised by folding said flexible side flaps substantially along said coloured indications. The coloured indications may thus not only indicate the presence of the side barriers to the user, but also indicate a folding line for folding the flexible side flaps. This can further assist the user in correctly positioning the article on their garment.

In embodiments according to the present disclosure, the flexible side flaps may each comprise a side portion of said backsheet and/or a side portion of said side layer. The side layer and the backsheet may be attached to each other, preferably along the outer edges of the side portions. The attachment of these layers to each other may have the effect in certain embodiments that upon folding of the side flaps, preferably along or in the vicinity of the seams, tension is created which may assist in raising the side barriers to the substantially upright position.

In embodiments according to the present disclosure, said side layers may each comprise a multiple layered section where the side layer is folded at least once, said multiple layered sections forming, or forming part of, said liquid side barriers. Such a multi-layer construction may strengthen the liquid side barriers and further reduce the risk of side-edge leakage.

In embodiments according to the present disclosure, the portions of the side layers, which form the liquid side barriers or part thereof, may extend over the full length of the article.

In embodiments according to the present disclosure, the loose portions of the side layers, which form the liquid side barriers or part thereof, may have a width in transverse direction T of the article ranging from 2.0 to 10.0 mm, preferably from 3.0 to 7.0 mm.

In embodiments according to the present disclosure, the liquid side barriers may consist entirely of or comprise non-elastic material, i.e. the need for elastic elements to ensure proper raising of the side barriers in use may be avoided.

In embodiments according to the present disclosure, the article may further comprise an acquisition layer positioned between said absorbent core and said topsheet.

In embodiments according to the present disclosure, the side layers may be, on each side, fixed to the respective longitudinal edge portion of the topsheet by means of a seam. The seams may be obtained by welding, such as ultrasonic welding, by applying a chemical compound such as an adhesive, by applying heat and/or pressure.

In a second aspect according to the present disclosure, which may be combined with the other aspects and embodiments described herein, a method is provided for manufacturing a disposable hygiene article comprising a liquid-permeable topsheet, a liquid-impermeable backsheet and an absorbent core arranged between said topsheet and said backsheet, the absorbent core defining a longitudinal centre axis which extends substantially in the middle of the core in longitudinal direction L of the article, and liquid side barriers arranged substantially along longitudinal edges of said absorbent core and provided to reduce side-edge leakage during use of said article, the method comprising a printing step by which a first coloured indication is printed on a garment facing side of said topsheet, said first coloured indication being located in an absorption area of the article in between longitudinal edge portions of the topsheet and being provided to indicate a wetting area to a user, and by which, in certain embodiments, preferably substantially simultaneously or at least in the same printing step, second coloured indications are printed on the garment facing side of said topsheet, said second coloured indications being located on said longitudinal edge portions of the topsheet and being provided to indicate the presence of said liquid side barriers to the user.

BRIEF DESCRIPTION OF THE DRAWINGS

The present disclosure will be discussed in more detail below, with reference to the attached drawings, in which.

DETAILED DESCRIPTION OF PARTICULAR EMBODIMENTS

Figure 1:
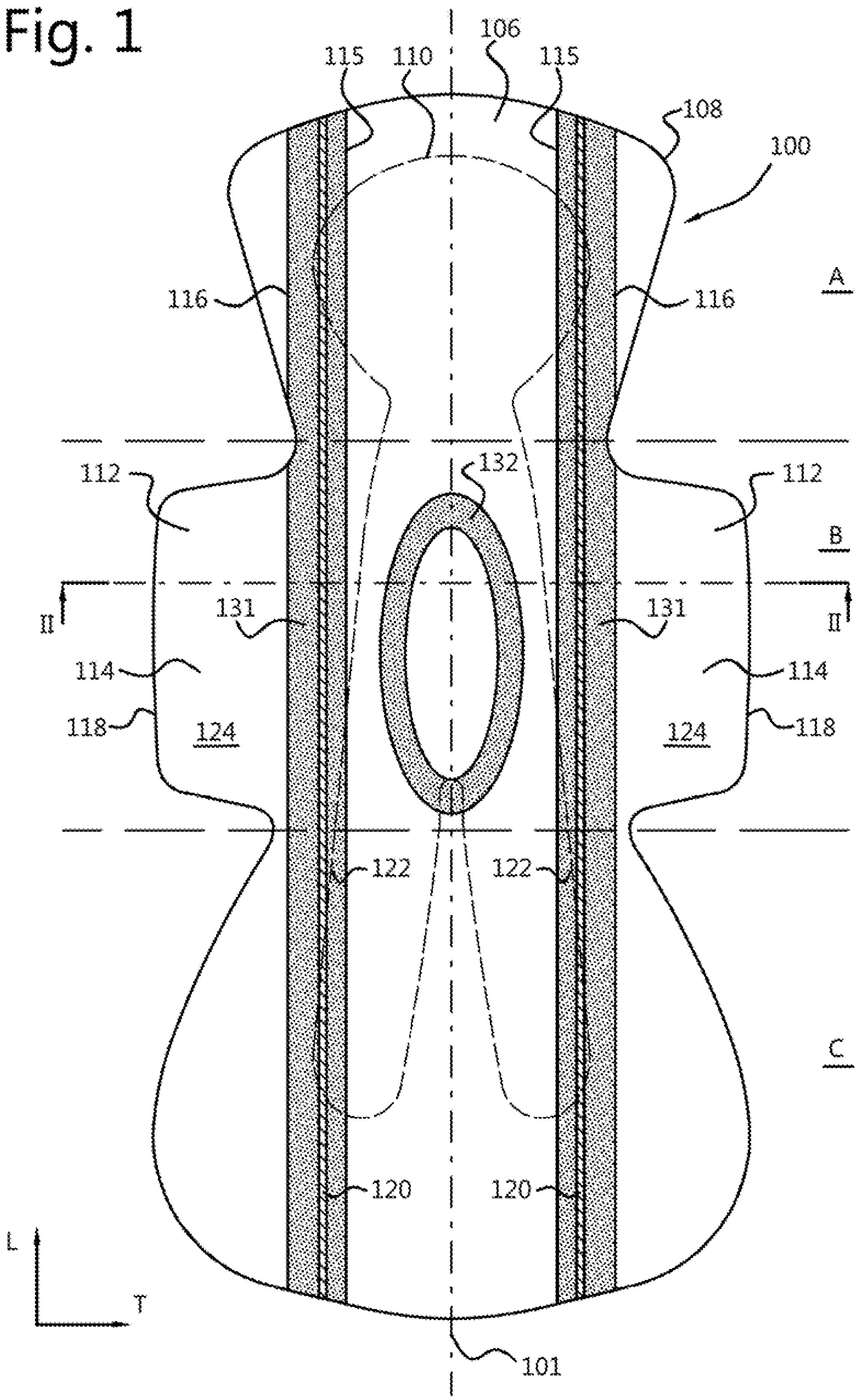
FIG. 1 shows a top view of a first embodiment of a disposable hygiene article according to the present disclosure.

The present disclosure will be described with respect to particular embodiments and with reference to certain drawings but the disclosure is not limited thereto but only by the claims. The drawings described are only schematic and are non-limiting. In the drawings, the size of some of the elements may be exaggerated and not drawn on scale for illustrative purposes. The dimensions and the relative dimensions do not necessarily correspond to actual reductions to practice of the disclosure.

Furthermore, the terms first, second, third and the like in the description and in the claims, are used for distinguishing between similar elements and not necessarily for describing a sequential or chronological order. The terms are interchangeable under appropriate circumstances and the embodiments of the disclosure can operate in other sequences than described or illustrated herein.

Moreover, the terms top, bottom, over, under and the like in the description and the claims are used for descriptive purposes and not necessarily for describing relative positions. The terms so used are interchangeable under appropriate circumstances and the embodiments of the disclosure described herein can operate in other orientations than described or illustrated herein.

Furthermore, the various embodiments, although referred to as "preferred" are to be construed as exemplary manners in which the disclosure may be implemented rather than as limiting the scope of the disclosure.

The term "comprising", used in the claims, should not be interpreted as being restricted to the elements or steps listed thereafter; it does not exclude other elements or steps. It needs to be interpreted as specifying the presence of the stated features, integers, steps or components as referred to, but does not preclude the presence or addition of one or more other features, integers, steps or components, or groups thereof. Thus, the scope of the expression "a device comprising A and B" should not be limited to devices consisting only of components A and B, rather with respect to the present disclosure, the only enumerated components of the device are A and B, and further the claim should be interpreted as including equivalents of those components.

Disposable hygiene articles are absorbent articles aimed for personal hygiene and are arranged to absorb body exudate, such as blood or urine. Such disposable hygiene articles are single-use articles and comprise for example adult incontinence articles, sanitary towels and panty liners.

Generally, the disposable hygiene articles are releasably attachable on a garment, suitably an undergarment of a user, by means of an adhesive material. A first embodiment is described with reference to FIGS. 1 and 2.

The article 100 has a body facing side intended to face the body of the user, in particular to face the body in the crotch area of the user, when the article is worn and a garment facing side intended to face the garment, in particular the undergarment or briefs, when the article is worn. FIG. 1 shows a view onto the article 100 from the body facing side.

The article 100 has a longitudinal direction L and a transverse direction T and has a longitudinal centre axis 101 which extends substantially in the middle of the absorbent part of the article. The article may be generally symmetrical with respect to this longitudinal centre axis, though this is not essential.

The article 100 may comprise a front portion A, a middle portion B and a rear portion C in the longitudinal direction L of the article. The front and rear portions A, C may be shaped to assist the user in optimally positioning the article 100 in their garment. The article 100 may be adapted for being folded in three with the front and rear portions A, C folded over the middle portion B when the article is individually packaged for delivery to a consumer. The article may be individually packaged by for example wrapping a thin plastic material around the article.

The disposable hygiene article 100 comprises a liquid-permeable topsheet 106, a liquid-impermeable backsheet 108 and an absorbent core 110, in certain embodiments preferably comprising an absorbent material. The liquid-permeable topsheet 106 is arranged at the body facing side of the article and is intended to be in contact with the body of the user, in particular with the crotch area of the user. The liquid-impermeable backsheet 108 is arranged at the garment facing side of the article and is intended to be in contact with the garment. The absorbent core 110 is arranged between and, in certain embodiments, preferably enclosed by the topsheet 106 and the backsheet 108. By liquid-permeable is meant that liquid, such as urine, blood or water, can pass through the material. By liquid-impermeable is meant that liquid, such as urine, blood or water, substantially cannot pass through the material. By absorbent material is meant material that is capable of absorbing or soaking up liquid, such as urine, blood or water.

Figure 6:
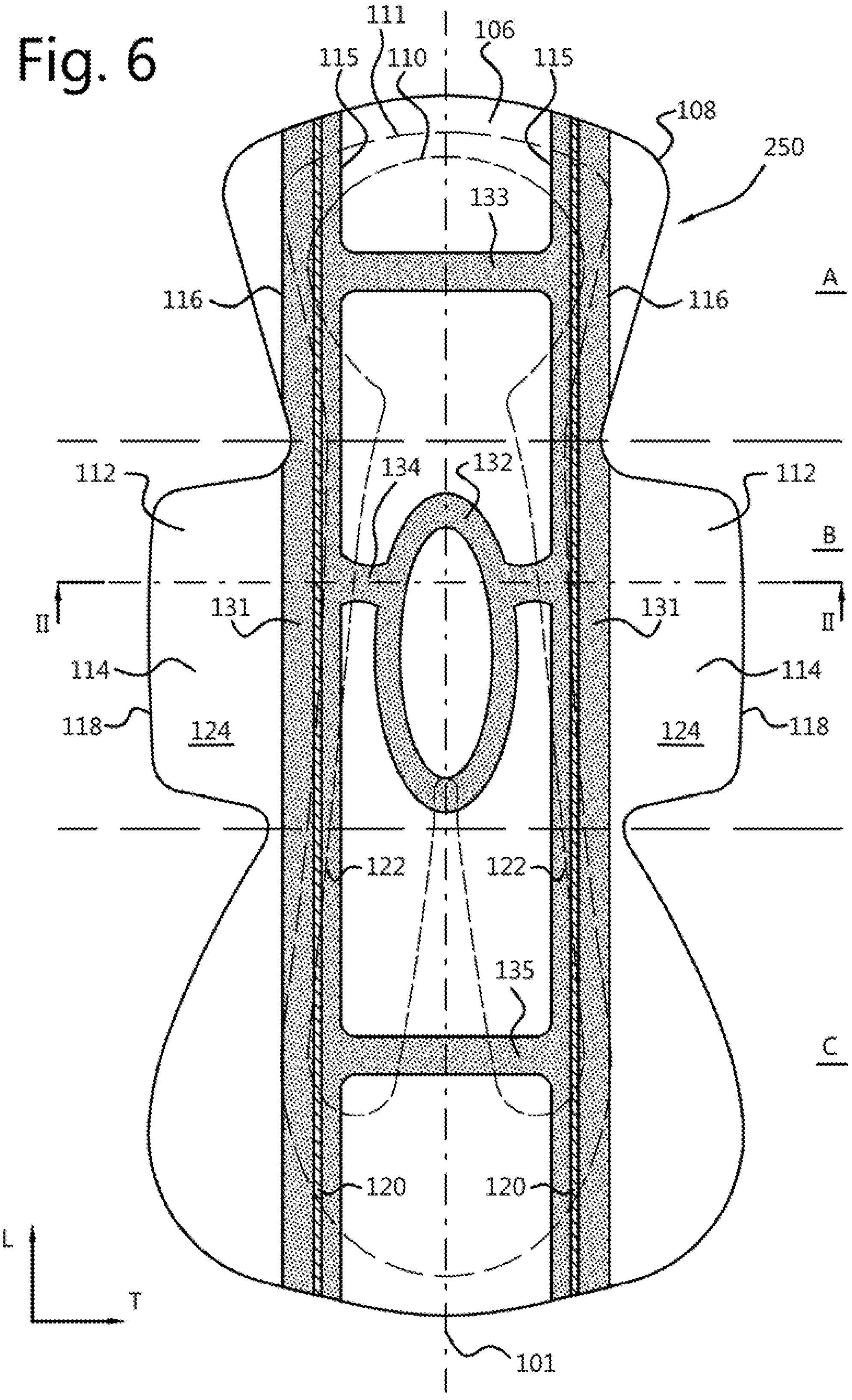
FIGS. 6 and 7 show a top view and a cross-sectional (exploded) view of another embodiment of a disposable hygiene article according to the present disclosure.
Figure 7:
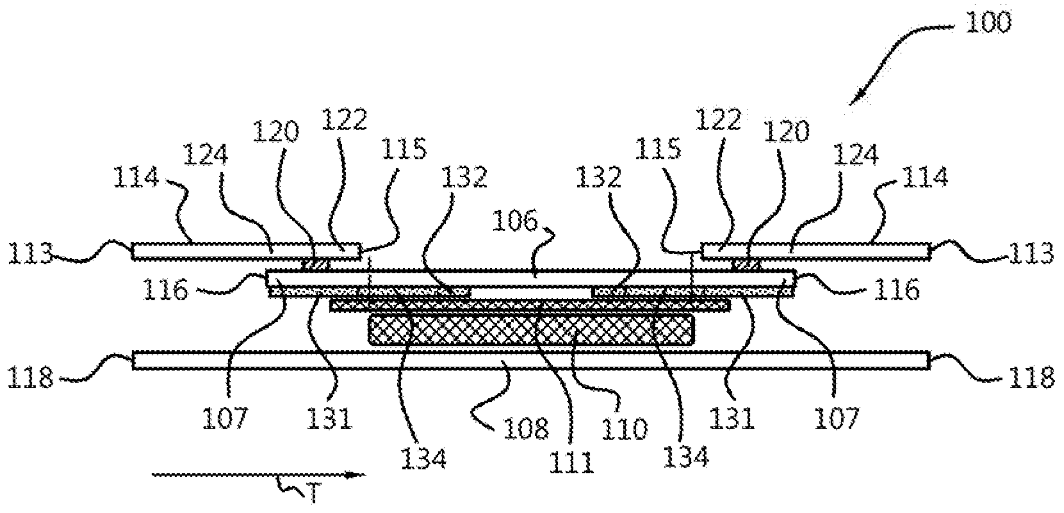

The article 100 may comprise further layers or sheets, such as an acquisition layer 111 (see FIGS. 6-7). An acquisition layer is preferably located beneath the topsheet 106, and is more preferably in contact with the garment facing side (i.e. the side facing the core 110) of the topsheet. The acquisition layer is intended to quickly absorb liquid and to spread the liquid before it is transported to the absorbent core, where it is retained. In certain embodiments, the acquisition layer preferably comprises an air-laid layer or wadding. The acquisition layer can be joined with the topsheet. The topsheet and the optional acquisition layer may be attached together by embossing, by using an adhesive or by means of ultrasonic processing to form a laminate. If the layers are attached together by means of ultrasonic processing, at least one of the topsheet or acquisition sheet comprises a thermoplastic material.

The other layers or sheets of the article 100 may be laminated together or the other layers may be attached together by means of embossing or adhesive. When laminated together the sheets are joined by means of a reinforcement executed with ultrasonic processing essentially along the peripheral edge of the sheets that forms an edge seal of the laminate so that the risk of any leakage and spread of liquid via the peripheral edge is minimized or eliminated. The reinforcement can extend from the periphery and towards the inside of the article for a distance of about 2-6 mm.

The topsheet 106 usually includes polyester or other synthetic polymer fibers, or films and is provided on the body facing side of the hygiene article. The topsheet is provided for comfort and conformability and for directing the liquid to the underlying absorbent core. In certain embodiments, the liquid-permeable topsheet 106 is preferably manufactured from a material that exhibits characteristics such as dryness and softness during the time when the absorbent article is being worn, because the topsheet 106 is in contact with the user's body. It is also desirable for the topsheet 106 to have a soft and textile-like surface which remains dry, even in the event of repeated wetting. The topsheet 106 can consist of a nonwoven material, for example, with a soft and smooth surface, such as a spunbond material made from polypropylene fibres. A perforated, hydrophobic nonwoven material may be used in order to permit the surface that is closest to the user's body to be kept dry, in conjunction with which openings are formed in the material that are larger than the holes between the fibres in the material. In this way, liquid can be led down through the perforated openings in the topsheet to the subjacent absorbent core. Other examples of materials for the topsheet are perforated plastic films such as a perforated polyester film attached to a nonwoven sheet. The topsheet may also be manufactured from a spunbond nonwoven material, an air-through nonwoven material, a spunlace nonwoven (hydroentangled) material, a meltblown nonwoven material, or a combination of these, such as a SMS-material, which is a layered product including spunbond-meltblown-spunbond nonwoven materials. The raw material can be polypropylene (PP), polyethylene (PE) polyester (PET), polyamide (PA), or a combination of these. If a combination is used, this can be a mixture of fibres from different polymers, although each fibre can also include different polymers (e.g. PP/PE bi-component fibres or PP/PE copolymers). Where appropriate, the plastic film can consist of PE or PP, PET, PLA or amyl (or, for that matter, any other thermoplastic polymer), or a mixture or copolymers of the aforementioned polymers. In certain embodiments, the topsheet preferably comprises a spunbond material comprising polypropylene fibres which provide for optimal comfort and handleability of the article. Other suitable fibres for making the nonwoven material are for example natural fibres such as bamboo, cotton and flax.

In the embodiment shown in FIG. 1, the absorbent core 110 has a specific shape, however the absorbent core 110 may also have another shape, for example a simpler shape like rectangular or oval. The absorbent core 110 may be manufactured from a fibre material in the form of natural or synthetic fibres with absorbent characteristics, or a mixture of natural fibres and synthetic fibres or other absorbent materials of a previously disclosed kind that are suitable for use in, for example, sanitary towels, incontinence pads and panty liners. The absorbent core may comprise one or more layers of defibrillated cellulosic fibres, for example cellulose fluff pulp. Other materials, which may be used, are for example absorbing or wettable nonwoven materials, foam materials or synthetic fibre materials.

The absorbent core 110 may comprise superabsorbent materials or may be free of superabsorbent material. In case the absorbent core comprises superabsorbent materials, the amount of superabsorbent materials, in certain embodiments, ranges preferably between 1% and 30% by weight of the absorbent core. The superabsorbent material may be polymeric materials in the form of particles, fibres, flakes or the like, and the material possesses the ability to absorb and chemically bind liquid equivalent to several times their own weight to form an aqueous gel. This imparts a very high liquid-absorbent capacity to the finished hygiene article while the article is still soft and easy to handle and manufacture.

Different layers of the article 100 may be laminated together or may be attached together for example by means of embossing or by means of an adhesive. The side layers 112 are for example laminated or attached to the backsheet, for example by means of embossing or by means of an adhesive.

Figure 2:
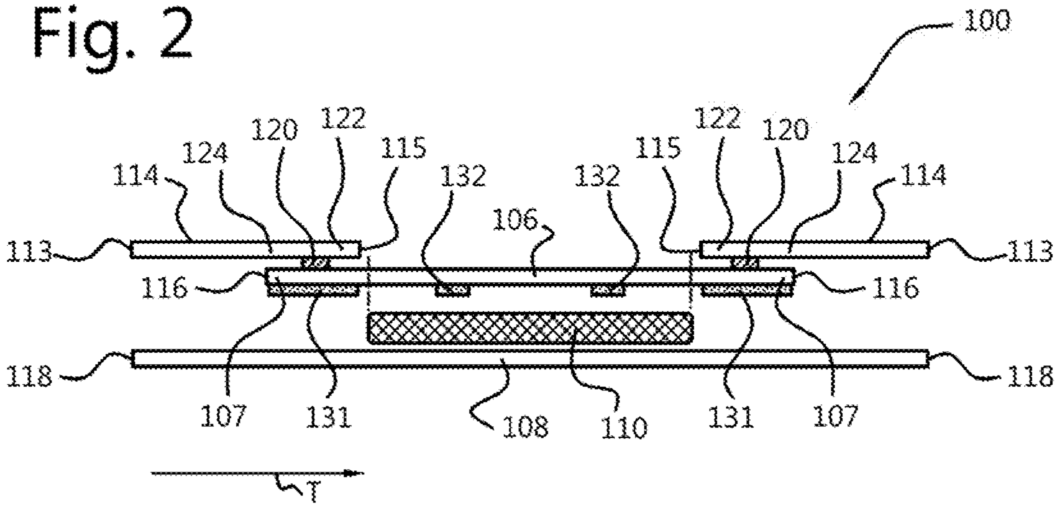
FIG. 2 is a cross-sectional (exploded) view of the article along the line II-II shown in FIG. 1.

In the embodiment shown in FIGS. 1 and 2, the topsheet 106 extends transversally, i.e. in the transverse direction T, from the longitudinal centre axis 101 beyond the edges of the absorbent core 110 (i.e. beyond the longitudinal side edges of the absorbent core 110) up to longitudinal side edges 116.

In the embodiment shown in FIGS. 1 and 2, the backsheet 108 extends transversally, i.e. in the transverse direction T, from the longitudinal centre axis 101 beyond the longitudinal side edges 116 of the topsheet 106. Preferably, at least in the middle portion B of the article 100, the backsheet 108 extends up to longitudinal side edges 118, so that the backsheet 108 has side portions which form a bottom layer of the flexible side flaps 112 on either side of the absorbent core 110. In the embodiment shown, the backsheet 108 also extends beyond the longitudinal side edges 116 of the topsheet 106 in the front and rear parts A and C, but this can be carried out differently.

In alternative embodiments, the longitudinal side edges 116 and 118 of the topsheet 106 and the backsheet 108 could coincide in the front part A and/or the rear part C and/or even in the middle part. In the latter case, the side flaps 112 may be formed by a single layer, namely the side layer 114 described herein, or by a combination of this side layer 114 and another layer.

In the embodiment shown in FIGS. 1 and 2, the flexible side flaps 112 comprise the side portions of the backsheet 108 and, on each side, a side layer 114. This side layer 114 extends transversally from an inner longitudinal edge 115 up to an outer longitudinal edge 113. The inner longitudinal edge 115 is, on each side, located between the longitudinal side edge 116 of the topsheet 106 and the centre axis 101, preferably closer to the longitudinal side edge 116 so as to cover only an edge portion of the absorbent part of the article. The side layer 114 may be attached to the topsheet 106 by means of a seam 120. This seam 120 partitions the side layer 114 in a first part 122 and a second part 124 with said first part 122 extending from the seam 120 towards the longitudinal centre axis 101 up to the inner longitudinal edge 115 and said second part 124 extending from the seam 120 away from the longitudinal centre axis 101 up to the outer longitudinal edge 113. The first part 122 extends above the topsheet 106 and is loose therefrom at least in the middle portion B of the article 100, and in use forms a liquid side barrier on the respective side of the absorbent part of the article.

In the embodiment shown in FIGS. 1 and 2, the seam 120 is located substantially in the middle of the area of overlap of the side layer 114 and the topsheet 106, i.e. substantially in the middle between the respective edges 115 and 116. In other embodiments, the seam may be located closer towards the one edge or the other. The first part 122, forming the liquid side barrier in use, preferably has a length, measured in transverse direction T, of 2.0 to 10.0 mm, preferably 3.0 to 7.0 mm.

In the embodiment shown in FIGS. 1 and 2, the topsheet 106 has longitudinal edge portions 107 which are provided with coloured indications 131 to indicate or highlight the presence of the liquid side barriers 122 to the user. This coloured indication 131 may be printed on the topsheet 106 underneath each of said first parts 122, possibly throughout the areas of overlap between the respective edges 115 and 116. This print may be provided on the garment facing side of the topsheet 106, possibly in the same process step as a further coloured indication 132 which is applied in the middle part of the topsheet 106 (where the absorbent core 110 is located).

In the embodiment shown in FIGS. 1 and 2, the coloured indications 131 are in use at least covered by the topsheet 106, in particular the longitudinal edge portions 107 thereof. The topsheet is, due to its liquid permeability, a layer of translucent material, i.e. the indications 131 and also the indication 132 are to a certain extent visible from above through the topsheet 106. The coloured indications 131 are in use furthermore at least partly covered by the side layers 114, which are preferably also translucent, so that the indications 131 are to a certain extent visible from above through (part of) the side layers 114 and the topsheet 106. The at least one layer which is/are located above the coloured indications 131 are translucent in such a way that the coloured indications are to some extent visible to the user through said layer(s).

In the embodiment shown in FIGS. 1 and 2, the side layer 114 is also present in the front and rear parts A and C, i.e. the seam 120 is a longitudinal seam extending over the full length of the article 100 in the longitudinal direction L. However, this is not essential.

The seam 120 can be obtained by any technique suitable to secure the side layer 114 to the topsheet 106 for example by welding, such as ultrasonic welding, by applying a chemical compound such as an adhesive, by applying heat and/or pressure.

In the embodiment shown in FIGS. 1 and 2, the outer longitudinal edge 113 of the side layer 114 coincides with the longitudinal side edge 118 of the backsheet 108 and these two layers are attached to each other along these edges 113, 118. This is preferred as this may simplify the manufacturing process (simultaneous cutting and attachment step), but is not essential.

In the embodiment shown in FIGS. 1 and 2, the article 100 comprises side flaps 112 which comprise the side layers 114 and side portions of the backsheet 108 which are attached to each other. These side flaps 112 or wings are configured for being folded about the garment to secure the position of the hygiene article 100 with respect to the garment. To this end, the flexible side flaps 112 may be suitably provided with a pressure sensitive adhesive provided on the garment facing side of the backsheet 108. Such adhesive may also be provided on the garment facing side of the backsheet 108 underneath the absorbent part of the article.

Figure 4:
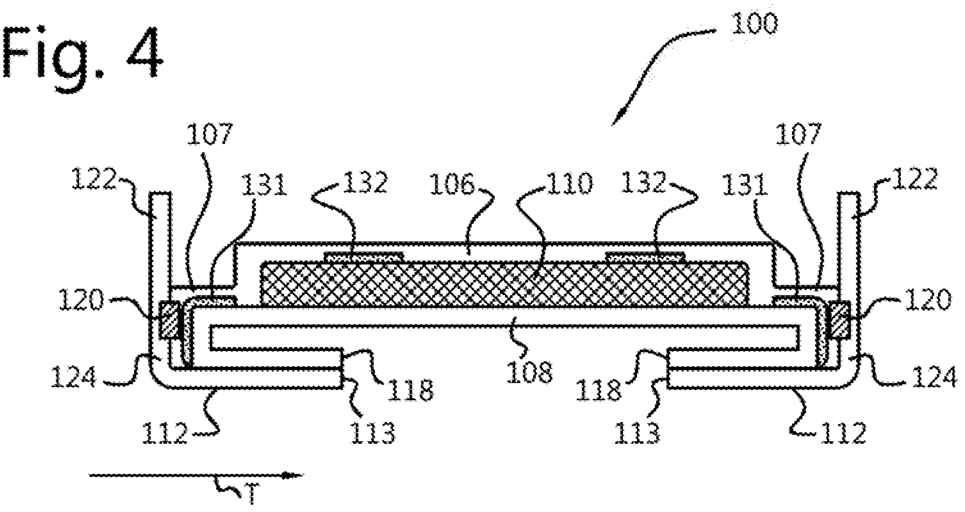
FIG. 4 is a cross-sectional view of the article of FIGS. 1 and 2 while in use.

In the embodiment shown in FIGS. 1 and 2, the side flaps 112 are intended to be folded substantially along the seam 120, or substantially along the coloured indications 131, as shown in FIG. 4, whereby the first parts 122 of the side layers 114 may be raised to a substantially upright position. The substantially upright position of these first parts 122 may enhance the functioning as barrier for the liquid. The movement to the substantially upright position may result from tension which is created by folding the side flaps 112. Thus, it may not be needed to provide elastic elements, such as for example elastic fibres or threads, in or on the material of the side layers 114 to achieve said movement, which may simplify the structure of the article 100. However, in alternative embodiments, such elastic elements may be applied to ensure or improve the raising of the side barriers 122.

Figure 3:
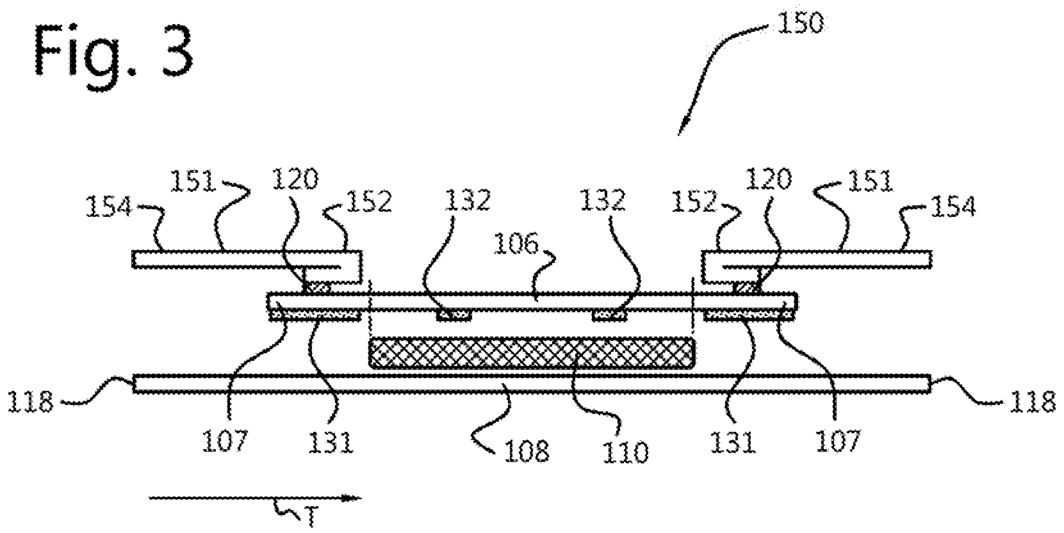
FIG. 3 is a cross-sectional (exploded) view of a second embodiment of a disposable hygiene article according to the present disclosure.

FIG. 3 shows an alternative embodiment of a disposable hygiene article 150 according to the present disclosure. This embodiment is in many aspects the same as that of FIGS. 1 and 2 and like parts are indicated with like reference numbers, so only the differences will be discussed here. In this embodiment, the side flaps comprise, on each side, a side portion of the backsheet 108 and a side layer 151 which is partitioned by the seam 120 into a first part 152 and a second part 154. In this embodiment, the first part 152 is a folded part of the side layer 151, such that the first part 152 comprises two layers of the material, which may create a stronger side barrier in use. In alternative embodiments, the folded part may also extend further, i.e. outwards beyond the seam 120, or the side layer may be entirely formed by two layers of the material, folded at the inner longitudinal edge, or the side layer 151 may be folded multiple times to create a multi-layer side barrier 152, for example a Z-folded part.

Figure 5:
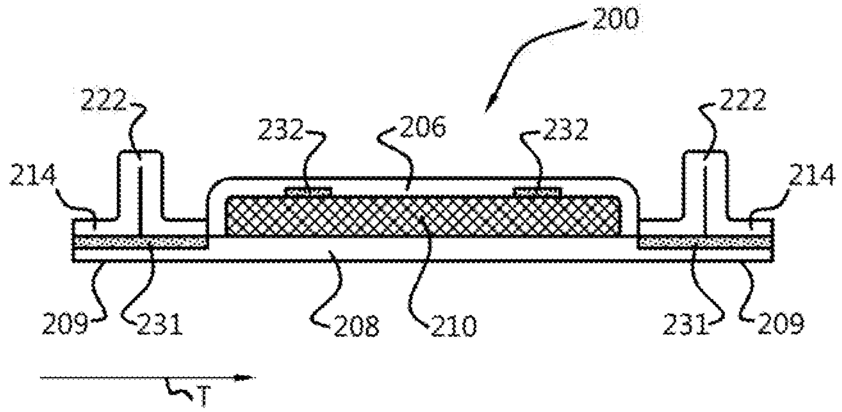
FIG. 5 is a cross-sectional view of a third embodiment of a disposable hygiene article according to the present disclosure.

FIG. 5 shows yet another embodiment of a disposable hygiene article 200 according to the present disclosure. This embodiment comprises, similar to the embodiments of FIGS. 1-4, a liquid permeable topsheet 206, a liquid-impermeable backsheet 208 and an absorbent core 210 arranged between the topsheet and the backsheet. The topsheet 206, backsheet 208 and core 210 may be structurally the same as described above for the other embodiments. The topsheet 206 may likewise be provided with a printed coloured indication 232 on its garment facing side to indicate the wetting area.

In the embodiment of FIG. 5, the liquid side barriers 222 are formed by means of side layers 214 which extend adjacent the longitudinal edges of the topsheet 206, i.e. without overlap (although some overlap is possible as well). These side layers 214 comprise an upwards directed folded part to form the side barriers 222 and are attached to side portions 209 of the backsheet 208. In this embodiment, the coloured indications 231 to indicate the presence of the side barriers 222 are provided on the side portions 209 of the backsheet 208, preferably on the body facing side thereof. The side layers 214 are made of a translucent material, so that the indications 231 are visible through the side layer 214 from above.

FIGS. 6 and 7 show another embodiment of a disposable hygiene article 250 according to the present disclosure. This embodiment is in many aspects the same as that of FIGS. 1 and 2 and like parts are indicated with like reference numbers. A first difference is that the article 250 comprises an acquisition layer 111, as described elsewhere herein, located in between the topsheet 106 and the core 110. A second difference is that the coloured indications 131, 132 on the garment facing side of the topsheet 106 are connected, in particular in the front part A by a connection 133, in the middle part B by connections 134 and in the back part C by a connection 135. These connecting parts 133, 134, 135 are preferably likewise applied in the same printing step in which the first and second coloured indications 131, 132 are applied.

In all embodiments of FIGS. 1-7, the side layers 114, 151, 214 may comprise a hydrophobic material to further reduce the risk of side-edge leakage, although this is not essential. The side layers may for example comprise a hydrophobic non-woven material or a hydrophobic spunbond material. Furthermore a hydrophobic coating layer can be applied on the material of the side layer or the material of the side layer can be treated for example with surfactants to adjust its degree of hydrophilicity.

The invention claimed is:

1. A disposable hygiene article, comprising:

a liquid-permeable topsheet;

a liquid-impermeable backsheet;

an absorbent core arranged between said topsheet and said backsheet, the absorbent core defining a longitudinal centre axis which extends substantially in the middle of the core in a longitudinal direction of the article;

side flaps disposed on transverse sides of the absorbent core, and liquid side barriers arranged substantially along longitudinal edges of said absorbent core and provided to reduce side-edge leakage;

wherein each of the liquid side barriers is formed by a side layer, wherein a longitudinal edge of said side layer overlaps longitudinal edge of said backsheet, the longitudinal edges of the side layer and the backsheet being terminal ends thereof facing a transverse direction, wherein coloured indications are provided on the article along said liquid side barriers to indicate the presence of said liquid side barriers to a user, wherein coloured indications are positioned between said longitudinal edge of said side layer and said longitudinal edge of said backsheet, wherein said coloured indications are provided underneath at least one layer of translucent material so as to be visible through said at least one layer of translucent material while avoiding direct contact with the user's skin, wherein, in at least one longitudinal position including the side flaps, the coloured indications do not overlap the absorbent core, wherein said at least one layer of translucent material includes the topsheet.

2. The disposable hygiene article according to claim 1, wherein at least parts of said coloured indications are provided on longitudinal edge portions of said topsheet.

3. The disposable hygiene article according to claim 2, wherein said coloured indications are printed on a garment facing side of said topsheet, said topsheet forming a first layer of translucent material.

4. The disposable hygiene article according to claim 3, wherein a further coloured indication is printed on said garment facing side of said topsheet, said further coloured indication being located in an absorption area of the article in between said longitudinal edge portions of the topsheet and being provided to indicate a wetting area to the user.

5. The disposable hygiene article according to claim 1, wherein said coloured indications extend between opposite longitudinal edges of the side layer.

6. The disposable hygiene article according to claim 1, wherein the liquid side barriers consist entirely of non-elastic material.

7. The disposable hygiene article according to claim 1, wherein said article further comprises an acquisition layer positioned between said absorbent core and said topsheet.

8. The disposable hygiene article according to claim 1, further comprising:

a further coloured indication positioned such that, in at least one longitudinal position including the side flaps, an entirety of the further coloured indication overlaps the absorbent core.

9. A disposable hygiene article, comprising:

a liquid-preamble topsheet;

a liquid-impermeable backsheet;

an absorbent core arranged between said topsheet and said backsheet, the absorbent core defining a longitudinal centre axis which extends substantially in the middle of the core in a longitudinal direction of the article;

side flaps disposed on transverse sides of the absorbent core, and liquid side barriers arranged substantially along longitudinal edges of said absorbent core and provided to reduce side-edge leakage, wherein each of the liquid side barriers is formed by a side layer, wherein a longitudinal edge of said side layer overlaps a longitudinal edge of said backsheet, the longitudinal edges of the side layer and the backsheet being terminal ends thereof facing a transverse direction, wherein coloured indications are provided on the article along said liquid side barriers to indicate the presence of said liquid side barriers to a user, wherein said coloured indications are positioned between said backsheet and a longitudinal edge of said topsheet and overlapping the side layer, the longitudinal edge of the topsheet being a terminal end thereof facing a transverse direction, wherein said coloured indications are provided underneath at least one layer of translucent material so as to be visible through said at least one layer of translucent material while avoiding direct contact with the user's skin, wherein, in at least one longitudinal position including the side flaps, the coloured indications do not overlap the absorbent core, wherein said at least one layer of translucent material includes the topsheet.

10. The disposable hygiene article according to claim 9, wherein said side layers comprise, on each side, a portion which extends above the respective coloured indication, said portion forming a second layer of translucent material.

11. The disposable hygiene article according to claim 10, wherein said portions of said side layers extend above said topsheet while being loose therefrom.

12. The disposable hygiene article according to claim 11, wherein said portions form, or form part of, said liquid side barriers.

13. The disposable hygiene article according to claim 9, wherein said liquid side barriers are provided for being at least partly raised to a substantially upright position in use.

14. The disposable hygiene article according to claim 9, wherein the side flaps are flexible side flaps arranged on opposite sides of said absorbent core and provided for attaching said article to a garment.

15. The disposable hygiene article according to claim 14, wherein said side barriers are provided for being at least partly raised by folding said flexible side flaps to a position in which said hygiene article is secured to said garment.

16. The disposable hygiene article according to claim 9, wherein said side barriers are provided for being at least partly raised by folding said flexible side flaps substantially along said coloured indications.

17. The disposable hygiene article according to claim 9, wherein said side layers each comprise a multiple layered section where the side layer is folded at least once, said multiple layered sections forming, or forming part of, said liquid side barriers.

18. The disposable hygiene article according to claim 10, wherein said portions of said side layers, which form the liquid side barriers or part thereof, extend over the full length of the article.

19. The disposable hygiene article according to claim 10, wherein said portions of said side layers, which form the liquid side barriers or part thereof, have a width in transverse direction T of the article ranging from 2.0 to 10.0 mm.

20. A method for manufacturing a disposable hygiene article, wherein the hygiene article comprises:

a liquid-permeable topsheet, a liquid-impermeable backsheet, an absorbent core arranged between said topsheet and said backsheet, the absorbent core defining a longitudinal centre axis which extends substantially in the middle of the core in longitudinal direction (L) of the article, side flaps disposed on transverse sides of the absorbent core, and liquid side barriers including side layers arranged substantially along and overlapping outer longitudinal edges of said absorbent core and provided to reduce side-edge leakage during user of said article, wherein the method comprises:

a printing step by which a first coloured indication is printed on a garment facing side of said topsheet, said first coloured indication being located in an absorption area of the article, at an area of said top sheet in overlapping arrangement with one of said side layers and being provided to indicate a wetting area to a user, and wherein by said printing step second coloured indications are printed on the garment facing side of said topsheet, said second coloured indications being located on said longitudinal edge portions of the topsheet and being provided to indicate the presence of said liquid side barriers to the user, and wherein, in at least one longitudinal position including the side flaps, the second coloured indications do not overlap the absorbent core.

21. The disposable hygiene article according to claim 20, wherein said portions of said side layers, which form the liquid side barriers or part thereof, have a width in transverse direction T of the article ranging from 3.0 to 7.0 mm.

22. The method according to claim 20, wherein the first coloured indication is positioned such that, in at least one longitudinal position including the side flaps, an entirety of the first coloured indication overlaps the absorbent core.

* * * * *